(12) United States Patent
Stoessel et al.

(10) Patent No.: US 9,096,791 B2
(45) Date of Patent: Aug. 4, 2015

(54) METAL COMPLEXES

(75) Inventors: Philipp Stoessel, Frankfurt am Main (DE); Dominik Joosten, Frankfurt am Main (DE)

(73) Assignee: Merck Patent GmbH (DE)

( * ) Notice: Subject to any disclaimer, the term of this patent is extended or adjusted under 35 U.S.C. 154(b) by 183 days.

(21) Appl. No.: 13/809,933

(22) PCT Filed: Jun. 17, 2011

(86) PCT No.: PCT/EP2011/002987
§ 371 (c)(1),
(2), (4) Date: Jan. 14, 2013

(87) PCT Pub. No.: WO2012/007088
PCT Pub. Date: Jan. 19, 2012

(65) Prior Publication Data
US 2013/0116464 A1    May 9, 2013

(30) Foreign Application Priority Data

Jul. 16, 2010   (DE) .......................... 10 2010 027 319

(51) Int. Cl.
*C09K 11/06* (2006.01)
*C07F 15/00* (2006.01)
*C07C 291/10* (2006.01)
*C07F 1/00* (2006.01)
*H05B 33/14* (2006.01)
*H01L 51/00* (2006.01)
*H01L 51/50* (2006.01)

(52) U.S. Cl.
CPC .............. *C09K 11/06* (2013.01); *C07C 291/10* (2013.01); *C07F 1/00* (2013.01); *C07F 15/006* (2013.01); *C07F 15/0086* (2013.01); *H01L 51/0087* (2013.01); *H05B 33/14* (2013.01); *C09K 2211/185* (2013.01); *H01L 51/0059* (2013.01); *H01L 51/0072* (2013.01); *H01L 51/0073* (2013.01); *H01L 51/0094* (2013.01); *H01L 51/5016* (2013.01); *Y02E 10/549* (2013.01)

(58) Field of Classification Search
CPC ...... C07F 15/006; C07F 15/0086; C07F 1/00; C07C 291/10; C09K 11/06; C09K 2211/185; H01L 51/0087; H05B 33/14

USPC ...................... 556/22, 136; 313/502; 428/690
See application file for complete search history.

(56) References Cited

U.S. PATENT DOCUMENTS

| 4,169,030 A | 9/1979 | Gray et al. |
| 4,271,033 A | 6/1981 | Gray et al. |
| 2009/0111965 A1 | 4/2009 | Lee |
| 2011/0101327 A1 | 5/2011 | Stoessel et al. |

FOREIGN PATENT DOCUMENTS

WO    WO-2010015307 A1    2/2010

OTHER PUBLICATIONS

Uozumi, Yasuhiro, et al., "Cyclization of o-Allylstyrene via Hydrosilylation:Mechanistic Aspects of Hydrosilylation of Styrenes Catalyzed by Palladium—Phosphine Complexes", J. Org. Chem., vol. 63, (1998), pp. 6137-6140.
Molander, Gary A., et al., "Determining the Scope of the Lanthanide Mediated, Sequential Hydroamination/C—C Cyclization Reaction: Formation of Tricyclic and Tetracyclic Aromatic Nitrogen Heterocycles", Tetrahedron, vol. 59, (2003), pp. 10581-10591.
Snegaroff, Katia, et al., "Deprotonative Metalation of Substituted Benzenes and Heteroaromatics Using Amino/Alkyl Mixed Lithium—Zinc Combinations", Chem. Eur. J., vol. 16, (2010), pp. 8191-8201.
Sanders, Georgine M., et al., "Ring Opening and Ring Contraction in Reactions of Some Aminobromo- and Dibromoisoquinolines with Potassium Amide in Liquid Ammonia", Laboratory of Organic Chemistry of the Agricultural University, vol. 93, No. 11, (1974), pp. 298-300.
International Search Report for PCT/EP2011/002987 mailed Oct. 27, 2011.
Moigno et al., "Preparation, Molecular Structure, and Fundamental Vibrational Modes of the Dinuclear Complexes trans-[{RhX(PiPr3)2}2{μ-1,3-(CN)2C6H4}]", Inorg. Chem., vol. 334, pp. 355-364 (2002).
Vincente et al., "The First Metal Complexes Derived from 3,5-Diethynylpyridine, X-ray Crystal Structure of [(AuPTo3)2{μ-C°C)2Py}] (Py= Pyridine-3,5-diyl; To= p-Tolyl)", Organometallics, vol. 23, pp. 5707-5712 (2004).

*Primary Examiner* — Porfirio Nazario Gonzalez
(74) *Attorney, Agent, or Firm* — Drinker Biddle & Reath LLP

(57) ABSTRACT

The present invention relates to metal complexes of the formula (1) and to electronic devices, in particular organic electro-luminescent devices, comprising these metal complexes.

18 Claims, No Drawings

METAL COMPLEXES

CROSS-REFERENCE TO RELATED APPLICATIONS

This application is a national stage application (under 35 U.S.C. §371) of PCT/EP2011/002987, filed Jun. 17, 2011, which claims benefit of German application 10 2010 027 319.8, filed Jul. 16, 2010 which are both incorporated by reference.

The present application relates to luminescent metal complexes and to electronic devices, in particular organic electroluminescent devices, which comprise these metal complexes.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are frequently organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescent emitters. In accordance with the prior art, the triplet emitters employed in phosphorescent OLEDs are usually mononuclear iridium or platinum complexes. There is still a need for improvement in these compounds, in particular with respect to the lifetime, efficiency, operating voltage and stability of the complexes, in order to be able to employ them in long-lived electroluminescent devices, for example for televisions or computer monitors. There is still a need for improvement in phosphorescent metal complexes which emit in all emission colours.

The object of the present invention is therefore the provision of novel metal complexes and organic electroluminescent devices comprising these metal complexes. The metal complexes are employed here, in particular, as emitters in an emission layer.

Surprisingly, it has been found that certain dimeric metal complexes and organic electroluminescent devices comprising these dimeric metal complexes achieve this object. These metal complexes are very highly suitable for use as emitters in the emission layer of an organic electroluminescent device, where they result in significant improvements, in particular with respect to the lifetime and efficiency. This applies to phosphorescent electroluminescent devices which emit in all emission colours. The present invention therefore relates to these metal complexes and to organic electroluminescent devices which comprise these complexes.

The prior art discloses dimeric metal complexes for use in organic electroluminescent devices. WO 2010/006666 discloses dimeric metal complexes, in particular platinum complexes, for use in organic electroluminescent devices in which the metal atoms are bridged by P—C—P ligands, i.e. diphosphine ligands.

Furthermore, WO 2008/003464 discloses metal complexes, in particular platinum and palladium complexes, which contain isonitrile ligands for use in organic electroluminescent devices.

The present invention relates to a compound of the following formula (1),

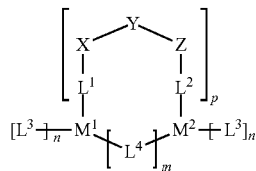

formula (1)

where the following applies to the symbols and indices used:

$M^1$, $M^2$ is on each occurrence, identically or differently, a metal selected from the group consisting of Pt, Pd, Ni, Ir, Rh, Cu, Ag, Au, Mo, W, Re, Ru or Os;

X, Y, Z is on each occurrence, identically or differently, CR or N;

$L^1$, $L^2$ is selected on each occurrence, identically or differently, from the group consisting of —NC, —CN, —NN, —NO, —NS, —CC and —C=CR;

$L^3$ is on each occurrence, identically or differently, a monodentate ligand or a bidentate ligand which is coordinated to one of the metal atoms $M^1$ or $M^2$;

$L^4$ is on each occurrence, identically or differently, a bidentate ligand which is simultaneously coordinated to both metal atoms $M^1$ and $M^2$;

R is on each occurrence, identically or differently, H, D, F, Cl, Br, I, $N(R^1)_2$, CN, $NO_2$, $Si(R^1)_3$, $B(OR)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more non-adjacent $CH_2$ groups may be replaced by $R^1C=CR^1$, $C\equiv C$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aralkyl or heteroaralkyl group having 5 to 40 aromatic ring atoms, which may in each case be substituted by one or more radicals $R^1$, or an aryloxy or heteroaryloxy group having 5 to 40 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two adjacent radicals R or one radical R with a radical $R^1$ here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$; two or more adjacent radicals $R^1$ or one radical $R^1$ with a radical R here may form a mono- or polycyclic, aliphatic or aromatic ring system with one another;

$R^2$ is on each occurrence, identically or differently, H, D, F, CN or an aliphatic, aromatic and/or heteroaromatic hydrocarbon radical having 1 to 20 C atoms, in which, in addition, one or more H atoms may be replaced by F; two or more substituents $R^2$ here may also form a mono- or polycyclic, aliphatic or aromatic ring system with one another;

m, n are on each occurrence, identically or differently, 0, 1, 2 or 3;

p is 1, 2, 3 or 4;

with the proviso that the indices m, n and p are selected so that the coordination number at each of the metals $M^1$ and $M^2$ is two, four or five.

The compound of the formula (1) may also be singly or multiply positively or negatively charged.

The coordination number of the metal arises from the number of groups which are coordinated to a metal atom, where a metal-metal bond or metal-metal interaction does not contribute to the coordination number.

In the definition above, the groups $L^1$, $L^2$, X, Y and Z are shown as neutral groups. However, it is also possible for them to be charged groups. In the ligand $L^1$-X—Y—Z-$L^2$, a single bond is in each case drawn in between $L^1$ and X, between X and Y, between Y and Z and between Z and $L^2$. However, this is merely intended to illustrate that a bond is present between these groups. However, it is not a single bond, but instead a bond whose bond order is between that of a single bond and that of a double bond. This may be illustrated with reference to the example of a ligand in which $L^1$ and $L^2$ each stand for —NC, i.e. for an isonitrile group, and X, Y and Z each stand for CR:

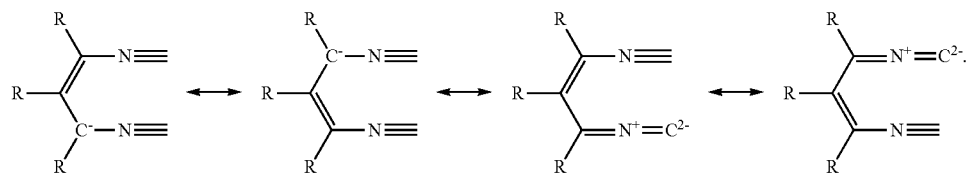

It can be seen here that these are mesomeric limit structures, where the bond can be indicated neither as a localised single bond nor as a localised double bond, but is instead between the bond order of a single bond and that of a double bond. The ligand here need not be neutral as such, but instead may also be charged, as in the example shown above, in which it is a singly negatively charged ligand.

The person skilled in the art of organometallic chemistry knows which metals usually have which coordination numbers. The coordination number is taken to mean the number of atoms coordinated to the metal. These are on the one hand the coordinating atoms of the groups $L^1$ and $L^2$ and on the other hand the coordinating atoms of the ligands $L^3$ and $L^4$. The usual coordination number around Pt(II), Pd(II), Ni(II), Ir(I) and Rh(I) is four, but may also be five. Furthermore, the usual coordination number around Cu(I), Ag(I) and Au(I) is two. Furthermore, the usual coordination number around Mo(0), W(0), Re(I), Ru(II) and Os(II) is five. Furthermore, the usual coordination number around Au(III) is four or five. In a preferred embodiment of the invention, m, n and p are therefore selected so that the coordination number around Pt, Pd, Ni, Ir and Rh is four and that the coordination number around Cu, Ag and Au(I) is two and that the coordination number around Mo, W, Re, Ru and Os is five and that the coordination number around Au(III) is four or five.

The ligand $L^4$ here is always coordinated to the metal atom $M^1$ via one atom and to the metal atom $M^2$ via one atom, where the coordinating atoms of the ligand $L^4$ can be the same atom which is simultaneously coordinated to $M^1$ and $M^2$, or different atoms. If the ligand $L^3$ is a monodentate ligand, it is coordinated to the metal $M^1$ or $M^2$ via one atom. If the ligand $L^3$ is a bidentate ligand, it is coordinated to one of the metals $M^1$ or $M^2$ via two atoms.

Suitable combinations of the ligands $L^3$ and $L^4$ in order to achieve the coordination number two are, for example:

p=1, n=0 and m=1; or
p=1, n=1 with $L^3$=monodentate ligand and m=0; or
p=2, n=0 and m=0.

Suitable combinations of the ligands $L^3$ and $L^4$ in order to achieve the coordination number four are, for example:

p=1, n=0 and m=3; or
p=1, n=1 with $L^3$=monodentate ligand and m=2; or
p=1, n=2 with $L^3$=monodentate ligand and m=1; or
p=1, n=1 with $L^3$=bidentate ligand and m=1; or
p=1, n=3 with $L^3$=monodentate ligand and m=0; or
p=1, n=2 with $L^3$=one monodentate and one bidentate ligand and m=0; or
p=2, n=0 and m=2; or
p=2, n=1 with $L^3$=monodentate ligand and m=1; or
p=2, n=2 with $L^3$=monodentate ligand and m=0; or
p=2, n=1 with $L^3$=bidentate ligand and m=0; or
p=3, n=1 with $L^3$=monodentate ligand and m=0; or
p=3, n=0 and m=1; or
p=4, n=0 and m=0.

Suitable combinations of the ligands $L^3$ and $L^4$ in order to achieve the coordination number five are, for example:

p=1, n=1 with $L^3$=monodentate ligand and m=3; or
p=1, n=2 with $L^3$=monodentate ligand and m=2; or
p=1, n=1 with $L^3$=bidentate ligand and m=3; or
p=1, n=3 with $L^3$=monodentate ligand and m=3; or
p=1, n=2 with $L^3$=one monodentate and one bidentate ligand and m=2; or
p=1, n=4 with $L^3$=monodentate ligand and m=0; or
p=1, n=2 with $L^3$=bidentate ligand and m=0; or
p=2, n=1 with $L^3$=monodentate ligand and m=2; or
p=2, n=2 with $L^3$=monodentate ligand and m=1; or
p=2, n=1 with $L^3$=bidentate ligand and m=1; or
p=2, n=3 with $L^3$=monodentate ligand and m=0; or
p=2, n=2 with $L^3$=one monodentate and one bidentate ligand and m=0; or
p=3, n=1 with $L^3$=monodentate ligand and m=1; or
p=3, n=2 with $L^3$=monodentate ligand and m=0; or
p=3, n=0 and m=2; or
p=4, n=1 with $L^3$=monodentate ligand and m=0; or
p=4, n=0 and m=1.

If the index p=2 and tetra- or pentacoordinated metals are involved, the ligands $L^1$-X—Y—Z-$L^2$ in the complex can be arranged in the cis-position or trans-position, as depicted diagrammatically below for complexes with tetracoordinated metals, each of which also contains further monodentate ligands $L^3$, where the ligands $L^1$-X—Y—Z-$L^2$ are in each case depicted by $L^1 \cap L^2$:

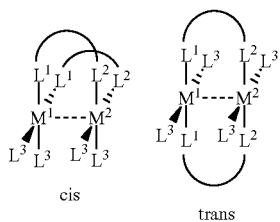

cis trans

If the ligands $L^3$ or at least one of the ligands $L^3$ stand for bidentate ligands, the ligands $L^1$-X—Y—Z-$L^2$ in complexes with tetracoordinated metals must be arranged in the cis-position. If the ligands $L^3$ are monodentate ligands, the complexes preferably have ligands in the trans-position.

The following definitions are used in the present application:

An aryl group in the sense of this invention contains 6 to 40 C atoms; a heteroaryl group in the sense of this invention contains 2 to 39 C atoms and at least one heteroatom, with the proviso that the sum of C atoms and heteroatoms is at least 5 and at most 40. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc. A cyclic carbene in the sense of this invention is a cyclic group which is bonded to the metal via a neutral C atom. The cyclic group here may be saturated or unsaturated. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group in the sense of this invention. An aralkyl group in the sense of this invention is taken to mean alkyl groups, in particular the alkyl groups mentioned below, which are substituted by an aryl or heteroaryl group, in particular one of the aryl or heteroaryl groups mentioned below.

An aromatic ring system in the sense of this invention contains 6 to 60 C atoms in the ring system. A heteroaromatic ring system in the sense of this invention contains 2 to 59 C atoms and at least one heteroatom in the ring system, with the proviso that the sum of C atoms and heteroatoms is at least 5 and at most 60. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit, such as, for example, a C, Si, N or O atom. Thus, for example, systems such as 9,9'-spirobifluorene, 9,9-diarylfluorene, triarylamine, diaryl ether, stilbene, etc., are also intended to be taken to mean aromatic ring systems in the sense of this invention, and likewise systems in which two or more aryl groups are interrupted, for example, by a linear or cyclic alkyl group or by a silyl group.

For the purposes of the present invention, a $C_1$- to $C_{40}$-alkyl group or $C_1$- to $C_{20}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, t-pentyl, 2-pentyl, neo-pentyl, cyclopentyl, n-hexyl, s-hexyl, t-hexyl, 2-hexyl, 3-hexyl, neohexyl, cyclohexyl, 2-methylpentyl, n-heptyl, 2-heptyl, 3-heptyl, 4-heptyl, cyclo-heptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)-octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl or cyclooctenyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the radicals R mentioned above and may be linked to the aromatic or hetero-aromatic group via any desired positions, is taken to mean, for example, groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

The compounds of the formula (1) can, as already described above, be charged or uncharged. If the compound of the formula (1) is charged, the charge is preferably +1, +2, +3, +4, −1, −2, −3 or −4, particularly preferably +1 or +2. In a preferred embodiment of the invention, the compounds of the formula (1) are uncharged, i.e. electrically neutral. This is achieved in a simple manner by the ligands $L^1$, $L^2$, $L^3$ and $L^4$ being selected in such a way that they compensate for the charges of the metal atoms $M^1$ and $M^2$.

If the compounds of the formula (1) are charged, they also contain one or more counterions. Examples of positively charged counterions, if the compound of the formula (1) is negatively charged, are alkali metal ions, alkaline-earth metal ions, tetraalkylammonium ions or tetraalkylphosphonium ions, where the alkyl group in each case preferably contains 1 to 4 C atoms. Examples of negatively charged counterions, if the compound of the formula (1) is positively charged, are F, Cl, Br, I, cyanide, hexafluorophosphate, tetrafluoroborate, tetraphenylborate, sulfate, phosphate or oxalate.

In a further embodiment of charged compounds of the formula (1), both the positively charged ion and also the negatively charged counterion is a compound of the formula (1).

The metals $M^1$ and $M^2$ in compounds of the formula (1) are preferably selected on each occurrence, identically or differently, from the group consisting of Pt(II), Pd(II), Ni(II), Ir(I), Rh(I), Cu(I), Ag(I), Au(I) and Au(III), where the indication in brackets in each case relates to the oxidation state of the metal. Particular preference is given to Pt(II), Pd(II) and Au(I).

Suitable combinations of the metals $M^1$ and $M^2$ are Pt(II)+Pt(II), Pt(II)+Pd(II), Pt(II)+Ni(II), Pt(II)+Ir(I), Pt(II)+Rh(I), Pt(II)+Au(III), Pt(II)+Cu(I), Pt(II)+Ag(I), Pt(II)+Au(I), Pd(II)+Pd(II), Pd(II)+Ni(II), Pd(II)+Ir(I), Pd(II)+Rh(I), Pd(II)+Au(III), Pd(II)+Cu(I), Pd(II)+Ag(I), Pd(II)+Au(I), Ni(II)+Ni(II), Ni(II)+Ir(I), Ni(II)+Rh(I), Ni(II)+Au(III), Ni(II)+Cu(I), Ni(II)+Ag(I), Ni(II)+Au(I), Ir(I)+Ir(I), Ir(I)+Rh(I), Ir(I)+Au(III), Ir(I)+Cu(I), Ir(I)+Ag(I), Ir(I)+Au(I), Rh(I)+Rh(I), Rh(I)+Au(III), Rh(I)+Cu(I), Rh(I)+Ag(I), Rh(I)+Au(I), Au(III)+Cu(I), Au(III)+Ag(I), Au(III)+Au(I), Cu(I)+Cu(I), Cu(I)+Ag(I), Cu(I)+Au(I), Ag(I)+Ag(I), Ag(I)+Au(I) and Au(I)+Au(I).

In a particularly preferred embodiment of the invention, $M^1$ and $M^2$ are selected identically. Particularly preferably, $M^1$ and $M^2$ are equal to Pt(II), or $M^1$ and $M^2$ are equal to Pd(II), or $M^1$ and $M^2$ are equal to Au(I).

The preferred embodiments of the ligands $L^1$-X—Y—Z-$L^2$ are described below:

The ligand $L^1$-X—Y—Z-$L^2$ can be cationic, neutral or anionic, depending on the choice of the groups $L^1$ and $L^2$ and X, Y and Z. In a preferred embodiment of the invention, the ligand $L^1$-X—Y—Z-$L^2$ is anionic, particularly preferably monoanionic. Very particularly preferably, each of the ligands $L^1$-X—Y—Z-$L^2$ in the compound of the formula (1) is monoanionic. This preference is due to the fact that an anionic ligand is able to compensate for the positive charges of $M^1$ and $M^2$.

In a preferred embodiment of the invention, a maximum of one of the groups X, Y and Z stands for N and the other two groups stand for CR. R here preferably stands for a group as described in detail below. If one of the groups X, Y or Z stands for N, it is preferably the group X or the group Z. In a preferred embodiment of the invention, the group Y stands for CR, particularly preferably for CH.

In a further preferred embodiment of the invention, the groups X and Z stand for CR. Particularly preferably, the groups X and Z stand for CR, and the group Y stands for CH.

As already defined above, the coordinating groups $L^1$ and $L^2$ are selected, identically or differently on each occurrence, from the group consisting of —NC, —CN, —NN, —NO, —NS, —CC and —C═CR.

In a preferred embodiment of the invention, the coordinating groups $L^1$ and $L^2$ are selected, identically or differently on each occurrence, from the group consisting of —NC, —NN, and —CC, particularly preferably —NC and —CC. Very particularly preferably, both groups $L^1$ and $L^2$ stand for —NC.

These groups may also carry charges. The groups —NC and —CN are neutral groups. The groups —NN, —CC and —C═CR are monoanionic groups.

In a preferred embodiment of the invention, the coordinating groups $L^1$ and $L^2$ are each the same groups.

In general, all of the above-mentioned embodiments of $L^1$, $L^2$, X, Y and Z can be combined with one another. Possible suitable embodiments are shown in Table 1 below.

TABLE 1

| $L^1$ | X | Y | Z | $L^2$ |
|---|---|---|---|---|
| NC | CR | CR | CR | NC |
| NC | CR | CR | CR | CN |
| NC | CR | CR | CR | NN |
| NC | CR | CR | CR | NO |
| NC | CR | CR | CR | NS |
| NC | CR | CR | CR | CC |
| NC | CR | CR | CR | C═CR |
| NC | CR | CR | N | NC |
| NC | CR | CR | N | CN |
| NC | CR | CR | N | NN |
| NC | CR | CR | N | NO |
| NC | CR | CR | N | NS |
| NC | CR | CR | N | CC |
| NC | CR | CR | N | C═CR |
| NC | CR | N | CR | NC |
| NC | CR | N | CR | CN |
| NC | CR | N | CR | NN |
| NC | CR | N | CR | NO |
| NC | CR | N | CR | NS |
| NC | CR | N | CR | CC |
| NC | CR | N | CR | C═CR |
| NC | N | CR | CR | NC |
| NC | N | CR | CR | CN |
| NC | N | CR | CR | NN |
| NC | N | CR | CR | NO |
| NC | N | CR | CR | NS |
| NC | N | CR | CR | CC |
| NC | N | CR | CR | C═CR |
| CN | CR | CR | CR | NC |
| CN | CR | CR | CR | CN |
| CN | CR | CR | CR | NN |
| CN | CR | CR | CR | NO |
| CN | CR | CR | CR | NS |
| CN | CR | CR | CR | CC |
| CN | CR | CR | CR | C═CR |
| CN | CR | CR | N | NC |
| CN | CR | CR | N | CN |
| CN | CR | CR | N | NN |
| CN | CR | CR | N | NO |
| CN | CR | CR | N | NS |
| CN | CR | CR | N | CC |
| CN | CR | CR | N | C═CR |
| CN | CR | N | CR | NC |
| CN | CR | N | CR | CN |
| CN | CR | N | CR | NN |
| CN | CR | N | CR | NO |
| CN | CR | N | CR | NS |
| CN | CR | N | CR | CC |
| CN | CR | N | CR | C═CR |
| CN | N | CR | CR | NC |
| CN | N | CR | CR | CN |
| CN | N | CR | CR | NN |
| CN | N | CR | CR | NO |
| CN | N | CR | CR | NS |
| CN | N | CR | CR | CC |
| CN | N | CR | CR | C═CR |
| NN | CR | CR | CR | NC |
| NN | CR | CR | CR | CN |
| NN | CR | CR | CR | NN |
| NN | CR | CR | CR | NO |
| NN | CR | CR | CR | NS |
| NN | CR | CR | CR | CC |
| NN | CR | CR | CR | C═CR |
| NN | CR | CR | N | NC |
| NN | CR | CR | N | CN |
| NN | CR | CR | N | NN |
| NN | CR | CR | N | NO |
| NN | CR | CR | N | NS |
| NN | CR | CR | N | CC |
| NN | CR | CR | N | C═CR |

TABLE 1-continued

| L¹ | X | Y | Z | L² |
|---|---|---|---|---|
| NN | CR | N | CR | NC |
| NN | CR | N | CR | CN |
| NN | CR | N | CR | NN |
| NN | CR | N | CR | NO |
| NN | CR | N | CR | NS |
| NN | CR | N | CR | CC |
| NN | CR | N | CR | C=CR |
| NN | N | CR | CR | NC |
| NN | N | CR | CR | CN |
| NN | N | CR | CR | NN |
| NN | N | CR | CR | NO |
| NN | N | CR | CR | NS |
| NN | N | CR | CR | CC |
| NN | N | CR | CR | C=CR |
| NO | CR | CR | CR | NC |
| NO | CR | CR | CR | CN |
| NO | CR | CR | CR | NN |
| NO | CR | CR | CR | NO |
| NO | CR | CR | CR | NS |
| NO | CR | CR | CR | CC |
| NO | CR | CR | CR | C=CR |
| NO | CR | CR | N | NC |
| NO | CR | CR | N | CN |
| NO | CR | CR | N | NN |
| NO | CR | CR | N | NO |
| NO | CR | CR | N | NS |
| NO | CR | CR | N | CC |
| NO | CR | CR | N | C=CR |
| NO | CR | N | CR | NC |
| NO | CR | N | CR | CN |
| NO | CR | N | CR | NN |
| NO | CR | N | CR | NO |
| NO | CR | N | CR | NS |
| NO | CR | N | CR | CC |
| NO | CR | N | CR | C=CR |
| NO | N | CR | CR | NC |
| NO | N | CR | CR | CN |
| NO | N | CR | CR | NN |
| NO | N | CR | CR | NO |
| NO | N | CR | CR | NS |
| NO | N | CR | CR | CC |
| NO | N | CR | CR | C=CR |
| NS | CR | CR | CR | NC |
| NS | CR | CR | CR | CN |
| NS | CR | CR | CR | NN |
| NS | CR | CR | CR | NO |
| NS | CR | CR | CR | NS |
| NS | CR | CR | CR | CC |
| NS | CR | CR | CR | C=CR |
| NS | CR | CR | N | NC |
| NS | CR | CR | N | CN |
| NS | CR | CR | N | NN |
| NS | CR | CR | N | NO |
| NS | CR | CR | N | NS |
| NS | CR | CR | N | CC |
| NS | CR | CR | N | C=CR |
| NS | CR | N | CR | NC |
| NS | CR | N | CR | CN |
| NS | CR | N | CR | NN |
| NS | CR | N | CR | NO |
| NS | CR | N | CR | NS |
| NS | CR | N | CR | CC |
| NS | CR | N | CR | C=CR |
| NS | N | CR | CR | NC |
| NS | N | CR | CR | CN |
| NS | N | CR | CR | NN |
| NS | N | CR | CR | NO |
| NS | N | CR | CR | NS |
| NS | N | CR | CR | CC |
| NS | N | CR | CR | C=CR |
| CC | CR | CR | CR | NC |
| CC | CR | CR | CR | CN |
| CC | CR | CR | CR | NN |
| CC | CR | CR | CR | NO |
| CC | CR | CR | CR | NS |
| CC | CR | CR | CR | CC |
| CC | CR | CR | CR | C=CR |
| CC | CR | CR | N | NC |
| CC | CR | CR | N | CN |
| CC | CR | CR | N | NN |
| CC | CR | CR | N | NO |
| CC | CR | CR | N | NS |
| CC | CR | CR | N | CC |
| CC | CR | CR | N | C=CR |
| CC | CR | N | CR | NC |
| CC | CR | N | CR | CN |
| CC | CR | N | CR | NN |
| CC | CR | N | CR | NO |
| CC | CR | N | CR | NS |
| CC | CR | N | CR | CC |
| CC | CR | N | CR | C=CR |
| CC | N | CR | CR | NC |
| CC | N | CR | CR | CN |
| CC | N | CR | CR | NN |
| CC | N | CR | CR | NO |
| CC | N | CR | CR | NS |
| CC | N | CR | CR | CC |
| CC | N | CR | CR | C=CR |
| C=CR | CR | CR | CR | NC |
| C=CR | CR | CR | CR | CN |
| C=CR | CR | CR | CR | NN |
| C=CR | CR | CR | CR | NO |
| C=CR | CR | CR | CR | NS |
| C=CR | CR | CR | CR | CC |
| C=CR | CR | CR | CR | C=CR |
| C=CR | CR | CR | N | NC |
| C=CR | CR | CR | N | CN |
| C=CR | CR | CR | N | NN |
| C=CR | CR | CR | N | NO |
| C=CR | CR | CR | N | NS |
| C=CR | CR | CR | N | CC |
| C=CR | CR | CR | N | C=CR |
| C=CR | CR | N | CR | NC |
| C=CR | CR | N | CR | CN |
| C=CR | CR | N | CR | NN |
| C=CR | CR | N | CR | NO |
| C=CR | CR | N | CR | NS |
| C=CR | CR | N | CR | CC |
| C=CR | CR | N | CR | C=CR |
| C=CR | N | CR | CR | NC |
| C=CR | N | CR | CR | CN |
| C=CR | N | CR | CR | NN |
| C=CR | N | CR | CR | NO |
| C=CR | N | CR | CR | NS |
| C=CR | N | CR | CR | CC |
| C=CR | N | CR | CR | C=CR |

Preferred ligands L¹-X—Y—Z-L² are the structures of the following formulae (2) to (12),

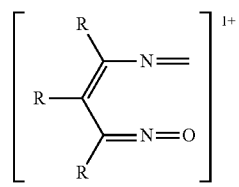

formula (2)

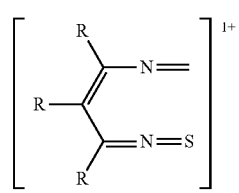

formula (3)

-continued formula (4)

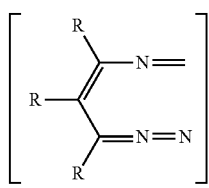

formula (5)

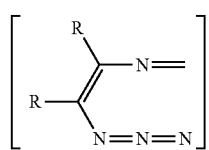

formula (6)

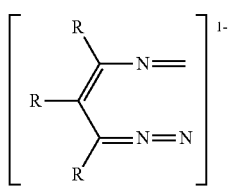

formula (7)

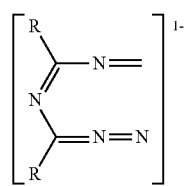

formula (8)

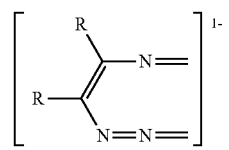

formula (9)

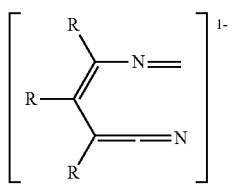

Formel (10)

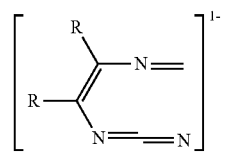

Formel (11)

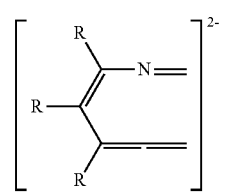

Formel (12)

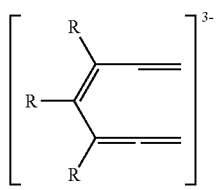

where R has the same meaning as defined above. The ligands of the formulae (2) and (3) are cationic ligands, the ligands of the formulae (4) and (5) are neutral ligands and the ligands of the formulae (6) to (12) are anionic ligands.

Particularly preferred ligands $L^1$-X—Y—Z-$L^2$ are the structures of the following formulae (2a) to (12a), formula (2a)

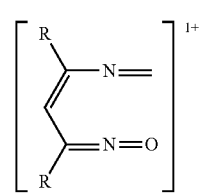

formula (3a)

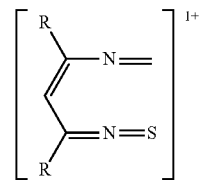

formula (4a)

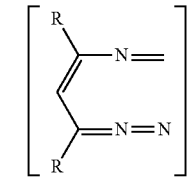

formula (5a)

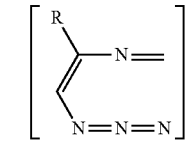

formula (6a)

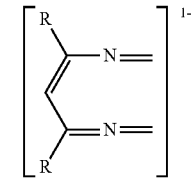

formula (7a)

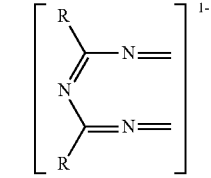

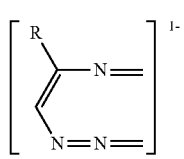

formula (8a)

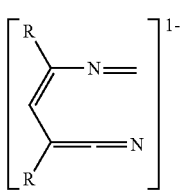

formula (9a)

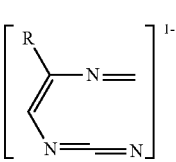

formula (10a)

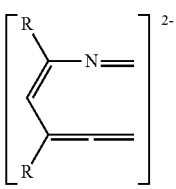

formula (11a)

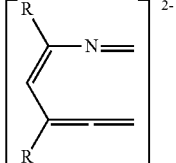

formula (12a)

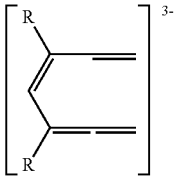

where R has the same meaning as defined above.

Particularly preferred ligands are the ligands of the above-mentioned formulae (6) and (9) or (6a) and (9a).

In a preferred embodiment of the invention, the radicals R which are bonded to X and Z are, if X or Z stands for CR, radicals which sterically screen the ligand. Preferred radicals R which are bonded to X and Z, if X or Z stands for CR, are therefore selected, identically or differently on each occurrence, from the group consisting of $Si(R^1)_3$, a straight-chain alkyl group having 1 to 20 C atoms or a straight-chain alkenyl or alkynyl group having 2 to 20 C atoms or a branched or cyclic alkyl, alkenyl or alkynyl group having 3 to 20 C atoms, each of which may be substituted by one or more radicals $R^1$, where one or more non-adjacent $CH_2$ groups may be replaced by $R^1C$=$CR^1$ or C≡C or O and where one or more H atoms may be replaced by D or F, or an aromatic or heteroaromatic ring system having 5 to 30 aromatic ring atoms, which may in each case be substituted by one or more radicals $R^1$, or an aralkyl or heteroalkyl group having 5 to 30 aromatic ring atoms, which may in each case be substituted by one or more radicals $R^1$; two adjacent radicals R or one radical R with a radical $R^1$ here may also form a mono- or polycyclic, aliphatic, aromatic and/or benzo-fused ring system with one another. In a particularly preferred embodiment of the invention, the radicals R which are bonded to X and Z are, if X or Z stand for CR, selected, identically or differently on each occurrence, from the group consisting of a straight-chain alkyl group having 1 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 24 aromatic ring atoms, which may in each case be substituted by one or more radicals $R^1$; two adjacent radicals R or one radical R with a radical $R^1$ here may also form a mono- or polycyclic, aliphatic, aromatic and/or benzo-fused ring system with one another. It is particularly preferred here for the radicals R which are bonded to X and Z to stand for sterically bulky radicals. Sterically bulky radicals are, for example, branched or cyclic alkyl groups having 3 to 10 C atoms, such as, for example, isopropyl, tert-butyl, neopentyl, adamantyl or cyclohexyl, or aromatic or heteroaromatic ring systems, as described above.

As described above, two or more adjacent radicals R may also form a ring with one another. This ring may then be aliphatic, aromatic and/or benzo-fused. If two or more adjacent radicals R form a ring with one another, it is preferred for it to be an aromatic ring, in particular a benzene ring, which may be substituted by one or more radicals $R^1$. A ring formation of this type is shown by way of example in the following formula (13). This is an embodiment of the formula (6). A further embodiment of the formula (6) are the formula (14) and (15) depicted below, in which, in addition to the ring formation of two adjacent radicals R, one radical R also forms a further ring with a radical $R^1$:

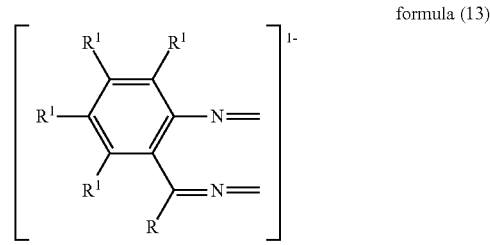

formula (13)

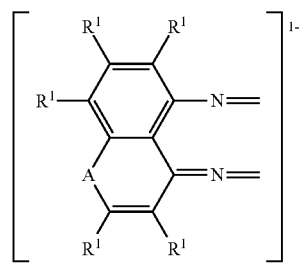

formula (14)

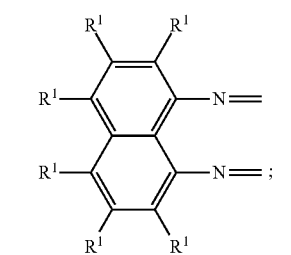

formula (15)

The symbols used here have the meanings given above and A stands for $C(R^2)_2$, O, S or $NR^2$.

In a further preferred embodiment of the invention, the complexes according to the invention contain at least two ligands of the formula $L^1$-X—Y—Z-$L^2$, particularly preferably four ligands of this type, if $M^1$ and $M^2$ do not stand for Cu(I), Ag(I) or Au(I). The index p therefore preferably stands for 2, 3 or 4, particularly preferably for 4.

The preferred embodiments of the invention given above and the preferred embodiments shown below can be combined with one another as desired.

In a particularly preferred embodiment of the invention, the preferences given above for the complexes according to the invention occur simultaneously. For particularly preferred complexes of the formula (1), the following therefore applies:

$M^1$, $M^2$ is selected, identically or differently on each occurrence, from the group consisting of Pt(II), Pd(II), Ni(II), Ir(I), Rh(I), Cu(I), Ag(I) and Au(I);

$L^1$-X—Y—Z-$L^2$ is an anionic ligand;

X, Y, Z is, identically or differently on each occurrence, CR or N, with the proviso that a maximum of one of the groups X, Y and Z stands for N;

$L^1$, $L^2$ is selected, identically or differently on each occurrence, from the group consisting of —NC, —NN and —CC;

R, if R, for X or Z=CR, is bonded to X or Z respectively, is selected, identically or differently on each occurrence, from the group consisting of Si($R^1$)$_3$, a straight-chain alkyl group having 1 to 20 C atoms or a straight-chain alkenyl or alkynyl group having 2 to 20 C atoms or a branched or cyclic alkyl, alkenyl or alkynyl group having 3 to 20 C atoms, each of which may be substituted by one or more radicals $R^1$, where one or more non-adjacent $CH_2$ groups may be replaced by $R^1$C=C$R^1$ or C≡C or O and where one or more H atoms may be replaced by D or F, or an aromatic or heteroaromatic ring system having 5 to 30 aromatic ring atoms, which may in each case be substituted by one or more radicals $R^1$, or an aralkyl or heteroaralkyl group having 5 to 30 aromatic ring atoms, which may in each case be substituted by one or more radicals $R^1$; two adjacent radicals R or one radical R with a radical $R^1$ here may also form a mono- or polycyclic, aliphatic, aromatic and/or benzo-fused ring system with one another;

p is 2, 3 or 4.

The other symbols and indices have the meanings shown above.

For very particularly preferred complexes of the formula (1), the following therefore applies:

$M^1$, $M^2$ is selected, identically or differently, preferably identically, on each occurrence, from the group consisting of Pt(II), Pd(II) and Au(I);

$L^1$-X—Y—Z-$L^2$ is a monoanionic ligand;

X, Z is, identically or differently on each occurrence, CR or N, with the proviso that a maximum of one group X or Z stands for N, preferably, identically or differently on each occurrence, CR;

Y is CR, preferably CH;

$L^1$, $L^2$ is selected, identically or differently on each occurrence, from the group consisting of —NC and —CC, preferably —NC;

R, if R, for X or Z=CR, is bonded to X or Z respectively, is selected, identically or differently on each occurrence, from the group consisting of a straight-chain alkyl group having 1 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 24 aromatic ring atoms, which may in each case be substituted by one or more radicals $R^1$; two adjacent radicals R or one radical R with a radical $R^1$ here may also form a mono- or polycyclic, aliphatic, aromatic and/or benzo-fused ring system with one another;

p is 2 if $M^1$ and/or $M^2$ is Au(I) and is 4 for all other $M^1$ and $M^2$.

The other symbols and indices have the meanings mentioned above.

The ligands $L^3$ and $L^4$ are preferably neutral, monoanionic, dianionic or trianionic ligands, particularly preferably neutral or monoanionic ligands, or, for the ligands $L^4$, also dianionic ligands. The ligands $L^3$ are monodentate or bidentate, i.e. have one or two coordination sites, and the ligands $L^4$ are bidentate, i.e. have two coordination sites that simultaneously coordinate to $M^1$ and $M^2$. If the ligand $L^3$ is bidentate, it coordinates to the same metal $M^1$ or $M^2$ with both coordination sites Suitable neutral, monodentate ligands $L^3$ are selected from carbon monoxide, nitrogen monoxide, isonitriles, such as, for example, tert-butyl iso-nitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, amines, such as, for example, trimethylamine, triethylamine, morpholine, phosphines, such as, for example, trifluoro-phosphine, trimethylphosphine, tri-cyclohexylphosphine, tri-tert-butyl-phosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclo-hexylarsine, tri-tert-butylarsine, triphenylarsinine, tris(pentafluorophenyl)-arsine, stibines, such as, for example, trifluorostibine, trimethylstibine, tri-cyclohexylstibine, tri-tert-butylstibine, triphenylstibine, tris(pentafluoro-phenyl)stibine, nitrogen-containing heterocycles, such as, for example, pyridine, pyridazine, pyrazine, pyrimidine, triazine, ethers, such as, for example, dimethyl ether, diethyl ether, aliphatic or aromatic sulfides, such as, for example, dimethyl sulfide, diethyl sulfide, or aliphatic or aromatic selenides, such as, for example, dimethyl selenide, diethyl selenide.

Suitable monoanionic, monodentate ligands $L^3$ are selected from hydride, deuteride, the halides F, Cl, Br and I, azide, alkylacetylides, such as, for example, methyl-C≡C$^-$, tert-butyl-C≡C$^-$, aryl- or heteroarylacetylides, such as, for example, phenyl-C≡C$^-$, alkyl, such as, for example, methyl, ethyl, n-propyl, i-propyl, n-butyl, s-butyl, t-butyl, aryl, such as, for example, phenyl, naphthyl, heteroaryl, such as, for example, pyridyl, hydroxide, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, iso-propanethiolate, tert-thiobutylate, thiophenolate, amides, such as, for example, dimethylamide, diethylamide, di-iso-propylamide, morpholide, carboxylates, such as, for example, acetate, trifluoro-acetate, propionate, benzoate, anionic, nitrogen-containing heterocycles, such as, for example, pyrrolide, imidazolide, pyrazolide, aliphatic or aromatic phosphides $PR_2^-$ or aliphatic or aromatic selenides $SeR^-$. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Suitable di- or trianionic ligands $L^3$ are $O^{2-}$, $S^{2-}$, nitrenes, which result in coordination in the form R—N=M, where R generally stands for a substituent, or $N^{3-}$.

Suitable neutral or mono- or dianionic bidentate ligands $L^3$ are selected from diamines, such as, for example, ethylenediamine, N,N,N',N'-tetra-methylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenyl-imino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]pyridine, 2-[1-(ethylimino)ethyl]pyridine, 2-[1-(iso-propylimino) ethyl]pyridine, 2-[1-(tert-butylimino)ethyl]pyridine, diimines, such as, for example, 1,2-bis(methyl-imino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethyl-imino)butane, 2,3-bis(iso-propylimino)butane, 2,3-bis(tert-butylimino)-butane, 1,2-bis(phenylimino) ethane, 1,2-bis(2-methylphenylimino)ethane, 1,2-bis(2,6-di-iso-propylphenylimino)ethane, 1,2-bis(2,6-di-tert-butylphenyl-imino)ethane, 2,3-bis(phenylimino)butane, 2,3-bis(2-methylphenylimino)-butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis-(dimethylphosphino) propane, bis(dimethylphosphino)butane, bis(diethylphosphino)methane, bis(diethylphosphino)ethane, bis (diethylphosphino)-propane, bis(diethylphosphino)butane, bis(di-tert-butylphosphino)methane, bis(di-tert-butylphosphino)ethane, bis(tert-butylphosphino)propane, bis(tert-butylphosphino)butane, 1,3-diketonates derived from 1,3-diketones, such as, for example, acetylacetone, tert-butylacetylacetone (2,2,6,6-tetramethyl-3,5-heptanedione), benzoylacetone, 1,5-diphenylacetyl-acetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethyl-glycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preference is furthermore given to bidentate monoanionic ligands $L^3$ which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals $R^1$. A multiplicity of such ligands is known to the person skilled in the art in the area of phosphorescent electroluminescent devices, and he will be able, without inventive step, to select further ligands of this type as ligand $L^3$ for compounds of the formula (1). The combination of two groups as depicted by the following formulae (16) to (43) is generally particularly suitable for this purpose. Combinations which are bonded via a neutral nitrogen atom or a carbene atom and via a negatively charged carbon atom or a negatively charged nitrogen atom, but also combinations in which, for example, two neutral nitrogen atoms or two negatively charged nitrogen atoms or two negatively charged carbon atoms are bonded to the metal, are generally suitable for this purpose. The bidentate ligand $L^3$ can then be formed from the groups of the formulae (5) to (32) by bonding these groups to one another in each case at the position denoted by #. The position at which the groups coordinate to the metal is denoted by *.

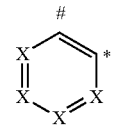

formula (16)

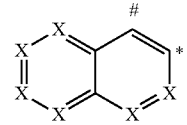

formula (17)

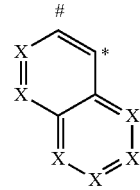

formula (18)

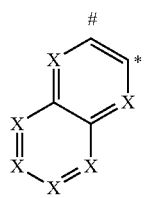

formula (19)

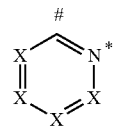

formula (20)

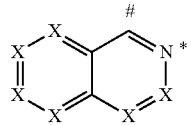

formula (21)

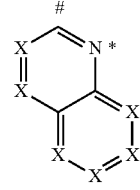

formula (22)

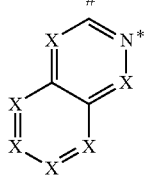

formula (23)

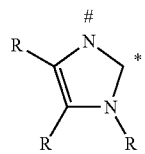

formula (24)

-continued

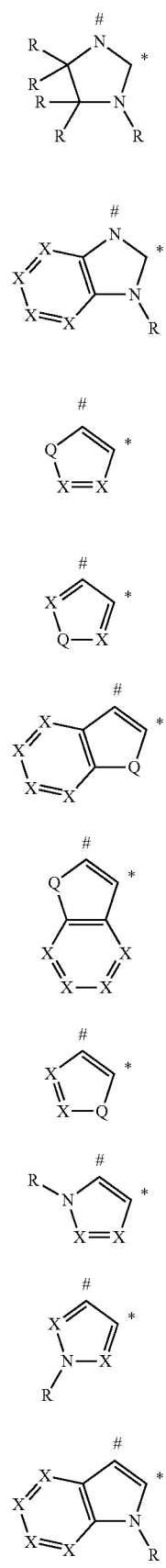

formula (25)

formula (26)

formula (27)

formula (28)

formula (29)

formula (30)

formula (31)

formula (32)

formula (33)

formula (34)

-continued

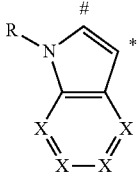

formula (35)

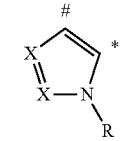

formula (36)

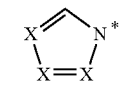

formula (37)

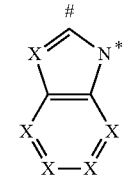

formula (38)

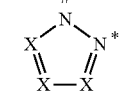

formula (39)

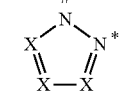

formula (40)

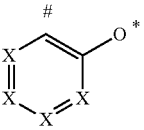

formula (41)

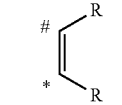

formula (42)

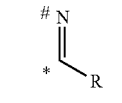

formula (43)

The symbols used have the same meaning as described above, with the proviso that a maximum of three symbols X in each group stand for N, and Q stands on each occurrence, identically or differently, for O or S. Preferably, a maximum of two symbols X in each group stand for N, particularly preferably a maximum of one symbol X in each group stands for N, very particularly preferably all symbols X stand for CR.

The groups of the formulae (16) to (43) are also suitable as monodentate ligands $L^3$. In this case, the position denoted by * is coordinated to the metal. The carbon atom at the position denoted by # is then replaced by a group X, i.e. a group CR or N.

Preferred ligands $L^3$ are ligands having a strong ligand field, in particular CN, CO, NO, phosphines, acetylides, isonitriles and carbenes.

Preferred bidentate ligands $L^4$ are selected from the group consisting of H, O, S, Se, CO, C≡N, NO, alkyl groups, in particular having 1 to 10 C atoms, C(=CR$_2$), —CR=CR—, ortho-phenylene, bisphosphides, bissulfides, bisphosphines, bisamines, bisamides, carbonate, thiocarbonate, isonitrile, acetylide or thiocarbonyl. Suitable diphosphines and diamines here are the corresponding ligands mentioned above in the case of $L^3$.

Furthermore suitable are ligands $L^4$ of the following formulae (44) to (51):

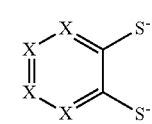

Formel (44)

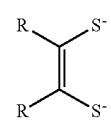

Formel (45)

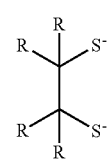

Formel (46)

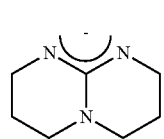

Formel (47)

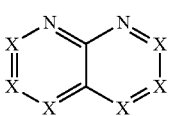

Formel (48)

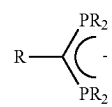

Formel (49)

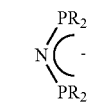

Formel (50)

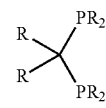

Formel (51)

where the symbols and indices used have the meanings mentioned above.

Preferred ligands $L^4$ are isonitriles, acetylides, bissulfides and CO.

The complexes of the formula (1) according to the invention are synthesised by reaction of the corresponding ligand or a ligand precursor with a suitable metal precursor. A suitable ligand precursor is, for example, a corresponding ligand which has not yet been deprotonated.

The present invention therefore furthermore relates to a process for the synthesis of a compound of the formula (1), by reaction of the free ligand or a corresponding ligand precursor with a suitable metal compound.

The complexes according to the invention can also serve as core of dendrimers. Furthermore, these complexes can be bonded into polymers. The linking to polymers can take place via reactive groups on the complexes, for example via alkenyl groups, allyl groups or siloxane groups.

Examples of preferred compounds of the formula (1) are compounds (1) to (38) depicted below. These complexes can be prepared, inter alia, using the synthetic methods explained above.

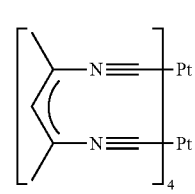

(1)

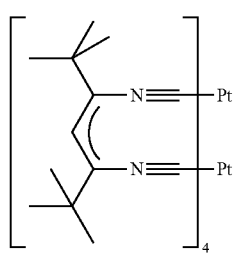

(2)

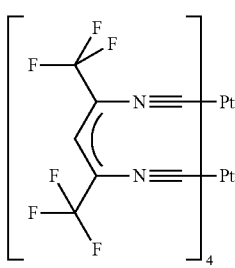

(3)

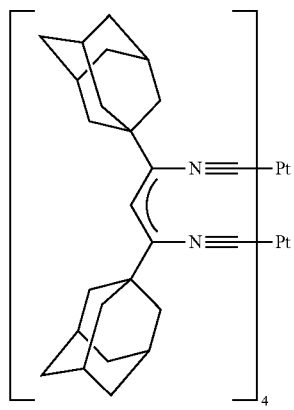

(4)

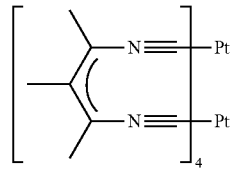

(5)

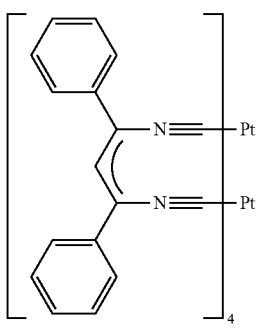
(6)
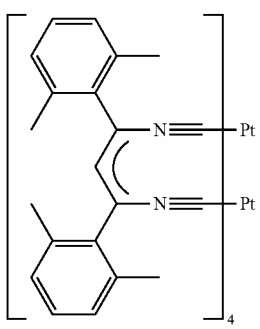
(7)
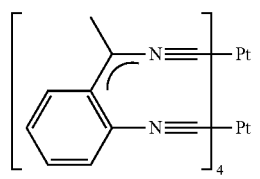
(8)
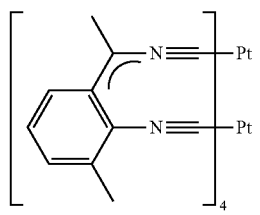
(9)
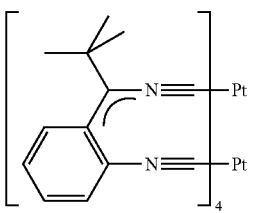
(10)
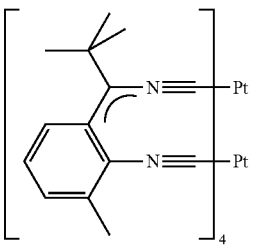
(11)
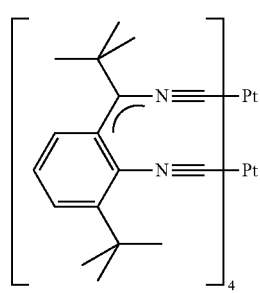
(12)
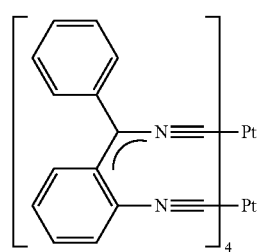
(13)
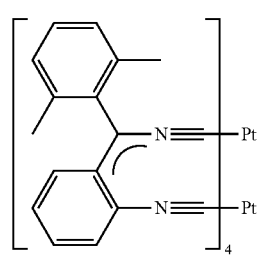
(14)
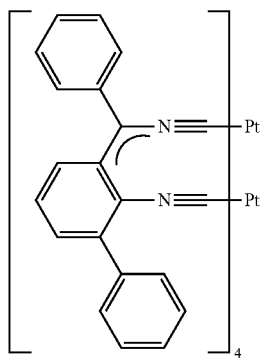
(15)
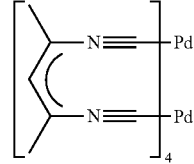
(16)
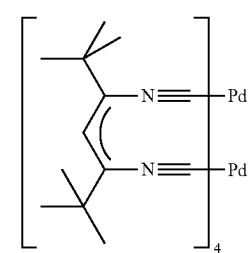
(17)

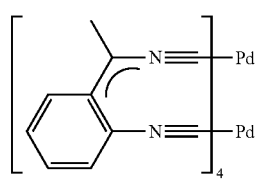 (18)
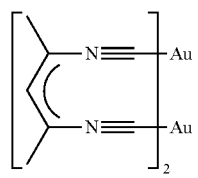 (19)
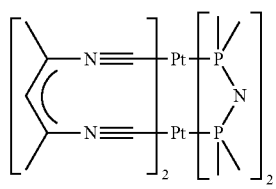 (20)
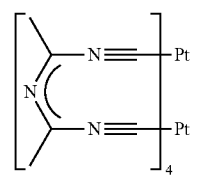 (21)
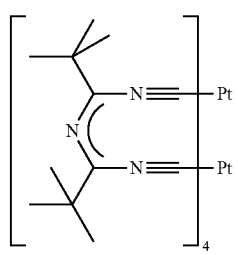 (22)
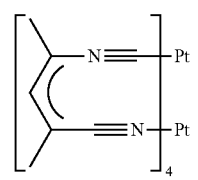 (23)
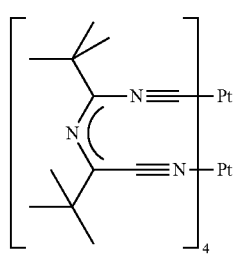 (24)
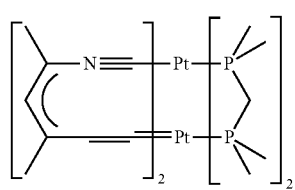 (25)
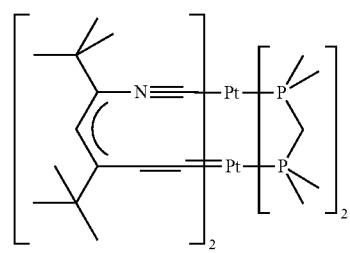 (26)
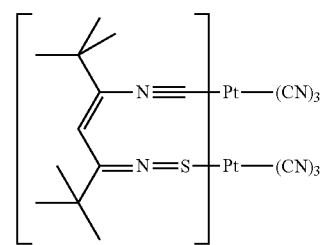 (27)
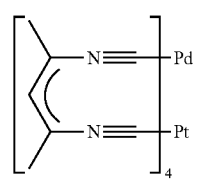 (28)
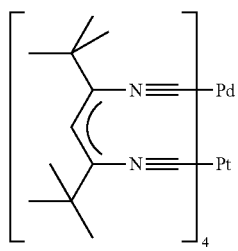 (29)
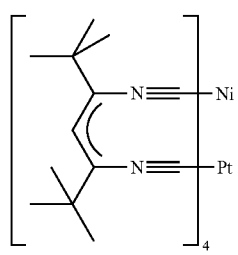 (30)
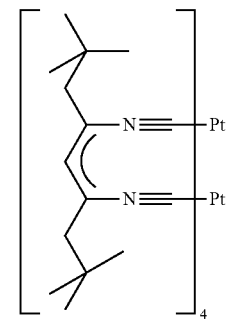 (31)

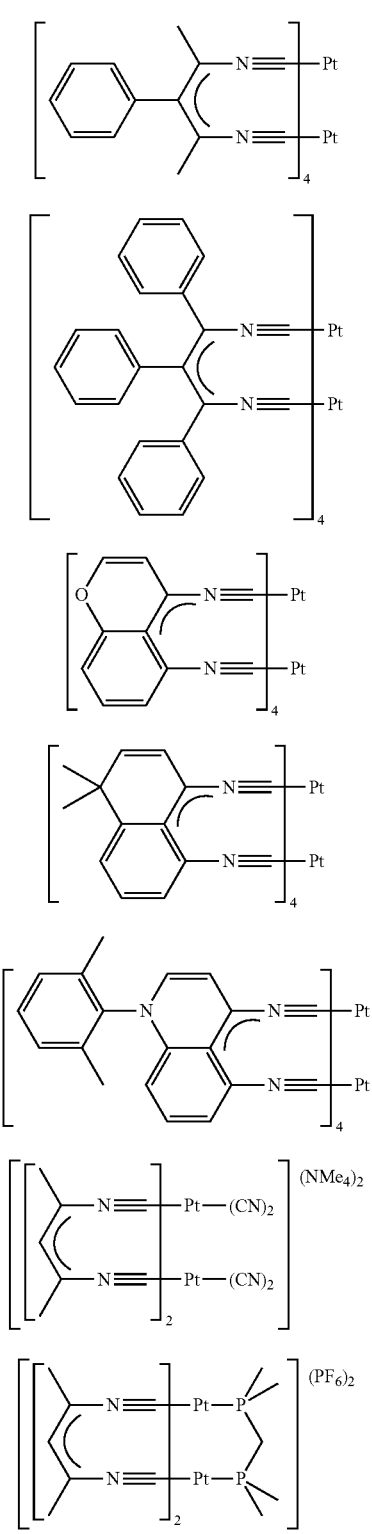

The complexes of the formula (1) described above or the preferred embodiments shown above can be used as active component in an electronic device. An electronic device is taken to mean a device which comprises anode, cathode and at least one layer, where this layer comprises at least one organic or organometallic compound. The electronic device according to the invention thus comprises anode, cathode and at least one layer which comprises at least one compound of the formula (1) shown above. Preferred electronic devices here are selected from the group consisting of organic electroluminescent devices (OLEDs, PLEDs), organic integrated circuits (O—ICs), organic field-effect transistors (O-FETs), organic thin-film transistors (O-TFTs), organic light-emitting transistors (O-LETs), organic solar cells (O—SCs), organic optical detectors, organic photoreceptors, organic field-quench devices (O-FQDs), light-emitting electrochemical cells (LECs) or organic laser diodes (O-lasers), comprising at least one compound of the formula (1) shown above in at least one layer. Particular preference is given to organic electroluminescent devices. Active components are in general the organic or inorganic materials which are introduced between anode and cathode, for example charge-injection, charge-transport or charge-blocking materials, but in particular emission materials and matrix materials. The compounds according to the invention exhibit particularly good properties as emission material in organic electroluminescent devices. A preferred embodiment of the invention are therefore organic electroluminescent devices comprising at least one compound of the formula (1) in an emission layer.

An organic electroluminescent device in the sense of this invention is taken to mean an electroluminescent device which comprises anode, cathode and at least one emitting layer, where at least one layer which is arranged between anode and cathode comprises at least one organic or organometallic compound or at least one metal coordination compound. The organic electroluminescent device according to the invention thus comprises anode, cathode and at least one emitting layer, where at least one layer comprises at least one compound of the formula (1) indicated above. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for interlayers which have, for example, an exciton-blocking function to be introduced between two emitting layers. However, it should be pointed out that each of these layers does not necessarily have to be present. The organic electroluminescent device here may comprise one emitting layer or a plurality of emitting layers, where at least one emitting layer comprises at least one compound of the formula (1). If a plurality of emission layers are present, they preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013). It is likewise possible, for the generation of white emission, for only one emission layer to be present and for two or more different emitters which emit in different emission colours to be present in this emission layer, where at least one compound of the formula (1) is present in the emission layer.

If the compound of the formula (1) is employed as emitting compound in an emitting layer, it is preferably employed in combination with one or more matrix materials. The mixture of the compound of the formula (1) and the matrix material comprises between 0.1 and 99% by vol., preferably between 1 and 90% by vol., particularly preferably between 3 and 40% by vol., in particular between 5 and 15% by vol., of the compound of the formula (1), based on the entire mixture of emitter and matrix material. The mixture correspondingly comprises between 99.9 and 1% by vol., preferably between 99 and 10% by vol., particularly preferably between 97 and 60% by vol., in particular between 95 and 85% by vol., of the matrix material, based on the entire mixture of emitter and matrix material.

Since the compounds of the formula (1) generally have high glass-transition temperatures, they are furthermore also suitable for use as pure layer without the use of a matrix material.

The matrix material employed can generally be all materials which are known for this purpose in the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 oder US 2009/0134784, indolocarbazole derivatives, for example in accordance with WO 07/063,754 or WO 08/056,746, indenocarbazole derivatives for example in accordance with the unpublished applications DE 102009023155.2 and DE 102009031021.5, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, or zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778 or the unpublished applications DE 102009048791.3 and DE 102010005697.9.

It may also be preferred to employ a plurality of different matrix materials as a mixture, in particular at least one electron-conducting matrix material and at least one hole-conducting matrix material. A preferred combination is, for example, the use of an aromatic ketone or a triazine derivative with a triarylamine derivative or a carbazole derivative as mixed matrix for the metal complex according to the invention. Preference is likewise given to the use of a mixture of a charge-transporting matrix material and an electrically inert matrix material which is not or not significantly involved in charge transport, as described, for example, in the unpublished application DE 102009014513.3.

In a further preferred embodiment of the invention, the compound of the formula (1) is used as co-host for a further phosphorescent compound which emits at longer wavelength. The phosphorescent compound which emits at longer wavelength can generally be any phosphorescent material as known from the prior art. Thus, a compound of the formula (1) which emits in the blue region can be employed as co-host for a green-phosphorescent compound, and a compound which emits in the green region can be employed as co-host for a red-phosphorescent compound. For the purposes of the present invention, all luminescent iridium, platinum and copper complexes are regarded as phosphorescent compounds. An electron-conducting matrix material is particularly preferably employed as further co-host. A device structure of this type is generally disclosed, for example, in the unpublished application DE 102008063470.0.

The compounds according to the invention can also be employed in other functions in the electronic device, for example as hole-transport material in a hole-injection or -transport layer, as charge-generation material or as electron-blocking material.

As cathode, preference is given to metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys of an alkali metal or alkaline-earth metal and silver, for example an alloy of magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example, Liq (lithium quinolinate), are likewise suitable for this purpose. The layer thickness of this layer is preferably between 0.5 and 5 nm.

As anode, preference is given to materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order either to facilitate irradiation of the organic material (O—SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing) ink-jet printing or nozzle printing. Since the compounds of the formula (1) generally have good solubility in the common organic solvents, they are highly suitable for processing from solution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer thereto by vacuum vapour deposition.

These processes are generally known to the person skilled in the art and can be applied by him without problems to organic electroluminescent devices comprising compounds of the formula (1) or the preferred embodiments mentioned above.

The organic electroluminescent devices according to the invention are distinguished by the following surprising advantages over the prior art:
1. The compounds of the formula (1) have both high thermal stability, are thus highly suitable for processing from the gas phase, but also have high solubility in a wide range of organic solvents and are therefore also very highly suitable for processing from solution.
2. Organic electroluminescent devices comprising compounds of the formula (1) as emitting materials have a very good lifetime.
3. depending on the structure of the ligands and the metal-metal separation in the complexes, compounds of the formula (1) are accessible which emit in all emission colours.
4. Blue-phosphorescent complexes are accessible which have a deep-blue emission colour and a long lifetime on use in organic electroluminescent devices. This is an advance over the prior art since to date there is still a need for improvement in blue-phosphorescent devices with respect to the colour coordinates and in particular the lifetime. In particular, the sharp emission bands of the compounds of the formula (1) which have no or virtually no vibronic structure result in very good and pure colour coordinates.
5. The organic electroluminescent devices according to the invention exhibit high efficiencies and steep current-voltage curves.

These above-mentioned advantages are not accompanied by an impairment in the other electronic properties.

The invention is explained in greater detail by the following examples without wishing to restrict it thereby. The person skilled in the art, without being inventive, will be able to carry out the invention throughout the disclosed range and thus prepare further complexes according to the invention or produce further organic electroluminescent devices according to the invention.

EXAMPLES

The following syntheses are carried out under a protective-gas atmosphere in dried solvents, unless indicated otherwise. The metal complexes are additionally handled with exclusion of light. The solvents and reagents can be purchased, for example, from Sigma-ALDRICH or ABCR. The indications in square brackets or the numerical indications in the case of the reagents relate to the CAS numbers.

Example 1

1-Isocyano-2-(isocyanomethyl)benzene

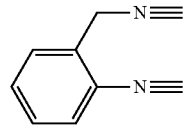

Procedure analogous to W. P. Weber et al., Angew. Chem., Int. Ed., 1972, 11, 6, 530. 17.6 ml (220 mmol) of chloroform, 500 mg of benzyltriethyl-ammonium chloride and then 60 ml of 50% by weight NaOH are added to a solution of 12.2 g (100 mmol) of 2-(aminomethyl)aniline [4403-69-4] in 100 ml of dichloromethane, and the mixture is stirred vigorously. After a short induction period, the mixture starts to boil. When the exothermic reaction has subsided, the mixture is stirred for a further 2 h, diluted with 300 ml of water and 200 ml of dichloromethane, the organic phase is separated off, washed once with 300 ml of water, once with 200 ml of saturated sodium chloride solution and then dried over potassium carbonate. After evaporation in vacuo, the oily residue is distilled twice in a bulb tube. Yield: 4.7 g (32 mmol), 32%, purity: about 97% (NMR).

Example 2

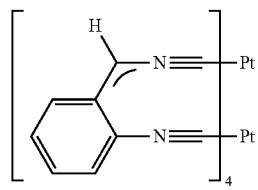

2.92 g (20 mmol) of 1-isocyano-2-(isocyanomethyl)benzene are added to a solution of 5.32 g (10 mmol) of tetrakis (isocyanomethane)platinum(II) bistetrafluoroborate [33989-89-8] in 100 ml of acetonitrile, and the mixture is stirred at 50° C. for 20 h. After cooling to room temperature, a solution of 641 mg (20 mmol) of sodium methoxide in 50 ml of methanol is added, and the mixture is stirred at room temperature for a further 2 h. The solvent is removed in vacuo, the residue is taken up in 100 ml of dichloro-methane, the suspension is filtered through a short Celite bed, the filtrate is evaporated to 5 ml and then covered with 30 ml of hexane. After standing for 40 h, the crystals are filtered off with suction, washed three times with 20 ml of hexane each time, dried in vacuo and then subjected to fractional sublimation in a high vacuum twice (p about $10^{-6}$ mbar, T about 300° C.). Yield: 2.13 g (2.2 mmol), 22%, purity: >99.5% (NMR).

Example 3

(Z)-3,5-Diisocyano-2,2,6,6-tetramethylhept-3-ene

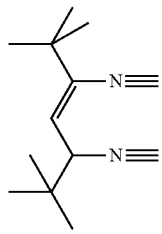

A mixture of 18.2 g (100 mmol) of (Z)-1-tert-butyl-3-imino-4,4-dimethyl-pent-1enylamine [146138-03-6], 242 ml (3 mol) of ethyl formate and 500 mg of sodium acetate is heated under reflux for 48 h. The excess ethyl formate and the ethanol formed are then distilled off, and the latter is removed completely by stirring the resultant oil in vacuo (0.1 mbar/T=25° C.) for 5 h. The oil is taken up in 200 ml of 1,2-dichloroethane, 9.8 ml (100 mmol) of carbon tetrachloride, 15.3 ml (110 mmol) of triethylamine and 55.2 g (210 mmol) of triphenylphosphine are added, the mixture is stirred at 65° C. for 4 h and then heated under reflux for 12 h. After cooling, the triethylammonium hydrochloride formed is filtered off with suction, rinsed with a little 1,2-dichloroethane, the 1,2-dichloroethane is removed in vacuo, the residue is taken up in 300 ml of cyclohexane, triphenylphosphine oxide is filtered off, the cyclohexane is removed in vacuo, and the residue is chromatographed on silica gel (cyclohexane:ethyl acetate, 9:1). Yield: 6.3 g (31 mmol), 31%, purity: about 95% (NMR).

The following ligands are prepared analogously:

| Ex. | Starting material | Ligand | Yield |
|---|---|---|---|
| 4 | 19796-84-0 | | 17% |
| 5 | 146138-02-5 | | 28% |
| 6 | 77953-70-9 | | 19% |
| 7 | 26954-44-9 | | 41% |

Example 8

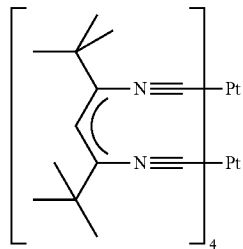

4.17 g (20 mmol) of (Z)-3,5-diisocyano-2,2,6,6-tetramethylhept-3-ene and 641 mg (20 mmol) of sodium methoxide are added to a solution of 5.32 g (10 mmol) of tetrakis(isocyanomethane)platinum(II) bistetrafluoroborate [33989-89-8] in 100 ml of acetonitrile, and the mixture is stirred at 50° C. for 20 h. The solvent is removed in vacuo, the residue is taken up in 100 ml of dichloromethane, the suspension is filtered through a short Celite bed, the filtrate is evaporated to a volume of 5 ml and then covered with 30 ml of heptane. After standing for 48 h, the crystals are filtered off with suction, washed three times with 20 ml of hexane each time, dried in vacuo and then subjected to fractional sublimation in a high vacuum twice (p about $10^{-6}$ mbar, T about 320° C.). Yield: 3.2 g (2.7 mmol), 27%, purity: >99.5% (NMR).

The following complexes are prepared analogously by reaction of the metal starting materials with the ligand, where the metal starting materials employed are the following compounds:

tetrakis(isocyanomethane)platinum(II) bistetrafluoroborate [33989-89-8]

tetrakis(isocyanomethane)palladium(II) bistetrafluoroborate [21797-13-7]

tetrakis(isocyanomethane)copper(I) perchlorate [14057-91-1]

bis(isocyanomethane)gold(I) tetrafluoroborate [100333-93-5]

cyclooctadienyl-bis(isocyanomethane)iridium(I) tetrafluoroborate [32679-03-1]

dichloro-(2,2-bis(diphenylphosphino)acetonitrile)platinum(II) [937025-36-0]

| Ex. | Ligand | Metal starting material | Complex | Yield |
|---|---|---|---|---|
| 9 | | [33989-89-8] | | 20% |
| 10 | | [33989-89-8] | | 23% |
| 11 | | [33989-89-8] | | 19% |
| 12 | | [33989-89-8] | | 26% |
| 13 | | [21797-13-7] | | 22% |

| Ex. | Ligand | Metal starting material | Complex | Yield |
|---|---|---|---|---|
| 14 | (diisocyanide ligand with tBu groups) | [14057-91-1] Use of 1 mol of ligand per mol of Cu | [Cu complex]$_2$ Complex was not sublimed | 28% |
| 15 | (diisocyanide ligand with tBu groups) | [100333-93-5] Use of 1 mol of ligand per mol of Au | [Au complex]$_2$ Complex was not sublimed | 15% |
| 16 | (diisocyanide ligand with tBu groups) | [32679-03-1] Use of 1 mol of ligand per mol of Ir | [Ir complex]$_2$ Complex was not sublimed | 25% |
| 17 | (diisocyanide ligand with tBu groups) | [937025-36-0] Use of 1 mol of ligand per mol of Pt | [Pt complex with Ph$_2$P-CH(CN)-PPh$_2$]$_2$ | 14% |

Production and Characterisation of Organic Electroluminescent Devices from the Gas Phase Electroluminescent devices according to the invention can be produced as described, for example, in WO 2005/003253.

The following device structure is used here:

| | |
|---|---|
| hole-injection layer (HIL) | 20 nm of 2,2',7,7'-tetrakis(di-para-tolylamino)-spiro-9,9'-bifluorene |
| hole-transport layer (HTL) | 5 nm of NPB (N-naphthyl-N-phenyl-4,4'-di-aminobiphenyl) |
| electron-blocking layer (EBL) | EBL1, 15 nm or EBL2, 15 nm |
| emission layer (EML) | matrix M1 or M2 or combinations thereof, 40 nm emitter: 10% by vol. doping |
| electron conductor (ETL) | 20 nm of BAlq |
| cathode | 1 nm of LiF, 100 nm of Al on top. |

The structures of EBL and M are depicted below for clarity:

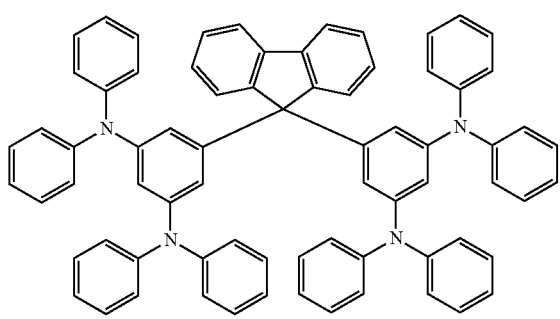

EBL1
WO 2009/124627

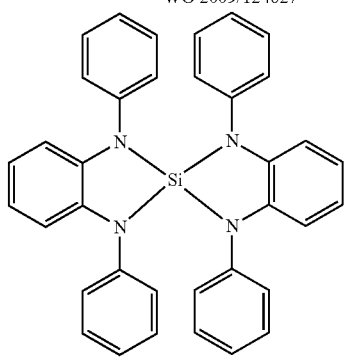

EBL2 and M3
WO 2010/054729

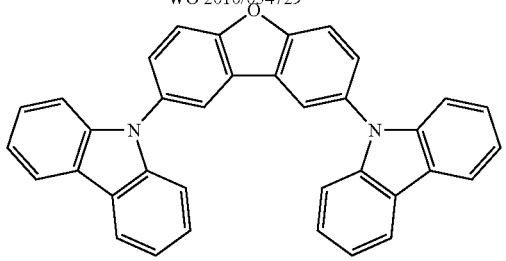

M1
CAS [913737-84-5]

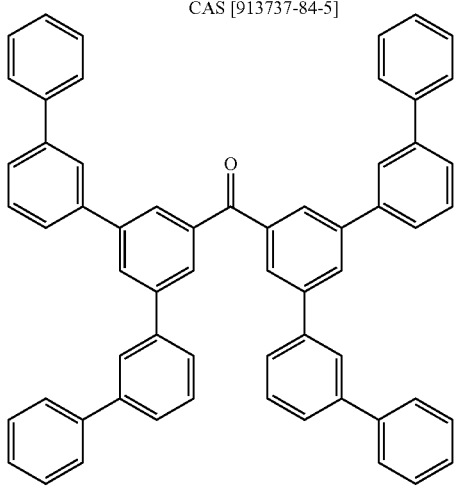

M2
WO 2010/006680

These as yet unoptimised OLEDs are characterised by standard methods; for this purpose, the electroluminescence spectra, the external quantum efficiency (measured in %) as a function of the luminance and the voltage (measured in V) from current/voltage/luminance characteristic lines (IUL characteristic lines) are determined.

TABLE 1

Device results

| Ex. | EBL | Matrix Emitter | EQE at 100 cd/m$^2$ [%] | Voltage at 100 cd/m$^2$ [V] | CIE x/y |
|---|---|---|---|---|---|
| 18 | EBL1 | M1 Example 2 | 3.1 | 6.3 | 0.15/0.42 |
| 19 | EBL2 | M2 Example 2 | 3.5 | 6.0 | 0.15/0.42 |
| 20 | EBL2 | M1 (30%) M2 (60%) Example 2 | 9.0 | 4.7 | 0.14/0.40 |
| 21 | EBL1 | M1 (20%) M2 (80%) Example 8 | 10.3 | 5.2 | 0.11/0.15 |
| 22 | EBL1 | M1 (30%) M2 (60%) Example 9 | 8.6 | 5.7 | 0.10/0.14 |
| 23 | EBL2 | M1 (40%) M2 (50%) Example 8 | 13.0 | 5.5 | 0.10/0.15 |
| 24 | EBL2 | M3 (70%) M2 (20%) Example 12 | 7.9 | 6.0 | 0.17/0.52 |
| 25 | EBL1 | M3 (60%) M2 (30%) Example 17 | 9.4 | 5.1 | 0.15.0.21 |

The invention claimed is:
1. A compound of the formula (1),

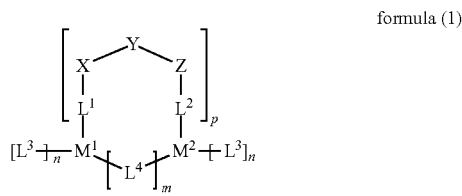

formula (1)

where the following applies to the symbols and indices used:

$M^1$ and $M^2$ is on each occurrence, identically or differently, a metal selected from the group consisting of Pt, Pd, Ni, Ir, Rh, Cu, Ag, Au, Mo, W, Re, Ru or Os;

X, Y and Z is on each occurrence, identically or differently, CR or N;

$L^1$ and $L^2$ is selected on each occurrence, identically or differently, from the group consisting of —NC, —CN, —NN, —NO, —NS, —CC and —C≡CR;

$L^3$ is on each occurrence, identically or differently, a monodentate ligand or a bidentate ligand which is coordinated to one of the metal atoms $M^1$ or $M^2$;

$L^4$ is on each occurrence, identically or differently, a bidentate ligand which is simultaneously coordinated to both metal atoms $M^1$ and $M^2$;

R is on each occurrence, identically or differently, H, D, F, Cl, Br, I, $N(R^1)_2$, CN, $NO_2$, $Si(R^1)_3$, $B(OR^1)_2$, C(=O)$R^1$, P(=O)$(R^1)_2$, S(=O)$R^1$, S(=O)$_2R^1$, $OSO_2R^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^1$, where one or more non-adjacent $CH_2$ groups is optionally replaced by $R^1$, $C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, or an aromatic or heteroaromatic ring system having 5 to 60 aromatic ring atoms, which optionally in each case be substituted by one or more radicals $R^1$, or an aralkyl or heteroaralkyl group having 5 to 40 aromatic ring atoms, which optionally in each case be substituted by one or more radicals $R^1$, or an aryloxy or heteroaryloxy group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; two adjacent radicals R or one radical R with a radical $R^1$ here may also form a mono- or polycyclic, aliphatic, aromatic and/or benzo-fused ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy or thioalkoxy group having 3 to 20 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$, and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two or more adjacent radicals $R^1$ or one radical $R^1$ with a radical R here may form a mono- or polycyclic, aliphatic or aromatic ring system with one another;

$R^2$ is on each occurrence, identically or differently, H, D, F, CN or an aliphatic, aromatic and/or heteroaromatic hydrocarbon radical having 1 to 20 C atoms, in which, in addition, one or more H atoms is optionally replaced by F; two or more substituents $R^2$ here may also form a mono- or polycyclic, aliphatic or aromatic ring system with one another;

m and n is on each occurrence, identically or differently, 0, 1, 2, or 3;

p is 1, 2, 3, or 4;

with the proviso that the indices m, n and p are selected so that the coordination number at each of the metals $M^1$ and $M^2$ is two, four or five.

2. The compound according to claim 1, wherein the following applies to p, n, m, $L^3$ and $L^4$ if the coordination number is 2:

p=1, n=0 and m=1; or
p=1, n=1 with $L^3$ =monodentate ligand and m=0; or
p=2, n=0 and m=0;

and in that the following applies to p, n, m, $L^3$ and $L^4$ if the coordination number is 4:

p=1, n=0 and m=3; or
p=1, n=1 with $L^3$ =monodentate ligand and m=2; or
p=1, n=2 with $L^3$ =monodentate ligand and m=1; or
p=1, n=1 with $L^3$ =bidentate ligand and m=1; or
p=1, n=3 with $L^3$ =monodentate ligand and m=0; or
p=1, n=2 with $L^3$ =one monodentate and one bidentate ligand and m=0; or
p=2, n=0 and m=2; or
p=2, n=1 with $L^3$ =monodentate ligand and m=1; or
p=2, n=2 with $L^3$ =monodentate ligand and m=0; or
p=2, n=1 with $L^3$ =bidentate ligand and m=0; or
p=3, n=1 with $L^3$ =monodentate ligand and m=0; or
p=3, n=0 and m=1; or
p=4, n=0 and m=0;

and in that the following applies to p, n, m, $L^3$ and $L^4$ if the coordination number is 5:

p=1, n=1 with $L^3$ =monodentate ligand and m=3; or
p=1, n=2 with $L^3$ =monodentate ligand and m=2; or
p=1, n=1 with $L^3$ =bidentate ligand and m=3; or
p=1, n=3 with $L^3$ =monodentate ligand and m=3; or
p=1, n=2 with $L^3$ =one monodentate and one bidentate ligand and m=2; or
p=1, n=4 with $L^3$ =monodentate ligand and m=0; or
p=1, n=2 with $L^3$ =bidentate ligand and m=0; or
p=2, n=1 with $L^3$ =monodentate ligand and m=2; or
p=2, n=2 with $L^3$ =monodentate ligand and m=1; or
p=2, n=1 with $L^3$ =bidentate ligand and m=1; or
p=2, n=3 with $L^3$ =monodentate ligand and m=0; or
p=2, n=2 with $L^3$ =one monodentate and one bidentate ligand and m=0; or
p=3, n=1 with $L^3$ =monodentate ligand and m=1; or
p=3, n=2 with $L^3$ =monodentate ligand and m=0; or
p=3, n=0 and m=2; or
p=4, n=1 with $L^3$ =monodentate ligand and m=0; or
p=4, n=0 and m=1.

3. The compound according to claim 1, wherein the compound is uncharged.

4. The compound according to claim 1, wherein the metals $M^1$ and $M^2$ are selected from the following combinations: Pt(II)+Pt(II), Pt(II)+Pd(II), Pt(II)+Ni(II), Pt(II)+Ir(I), Pt(II)+Rh(I), Pt(II)+Au(III), Pt(II)+Cu(I), Pt(II)+Ag(I), Pt(II)+Au(I), Pd(II)+Pd(II), Pd(II)+Ni(II), Pd(II)+Ir(I), Pd(II)+Rh(I), Pd(II)+Au(III), Pd(II)+Cu(I), Pd(II)+Ag(I), Pd(II)+Au(I), Ni(II)+Ni(II), Ni(II)+Ir(I), Ni(II)+Rh(I), Ni(II)+Au(III), Ni(II)+Cu(I), Ni(II)+Ag(I), Ni(II)+Au(I), Ir(I)+Ir(I), Ir(I)+Rh(I), Ir(I)+Au(III), Ir(I)+Cu(I), Ir(I)+Ag(I), Ir(I)+Au(I), Rh(I)+Rh(I), Rh(I)+Au(III), Rh(I)+Cu(I), Rh(I)+Ag(I), Rh(I)+Au(I), Au(III)+Cu(I), Au(III)+Ag(I), Au(III)+Au(I), Cu(I)+Cu(I), Cu(I)+Ag(I), Cu(I)+Au(I), Ag(I)+Ag(I), Ag(I)+Au(I) and Au(I)+Au(I).

5. The compound according to claim 1, wherein $M^1$ and $M^2$ are selected identically, equal to Pt(II) or equal to Pd(II) or equal to Au(I).

6. The compound according to claim 1, wherein a maximum of one of the groups X, Y and Z stands for N and the other two groups stand for CR.

7. The compound according to claim 1, wherein the groups X and Z stand, identically or differently on each occurrence, for CR and the group Y stands for CH.

8. The compound according to claim 1, wherein $L^1$ and $L^2$ are selected, identically or differently on each occurrence, from the group consisting of —NC, —NN, and —CC.

9. The compound according to claim 1, wherein $L^1$ and $L^2$ are identically or differently on each occurrence,—NC or —CC.

10. The compound according to claim 1, wherein the ligands $L^1$—X—Y—Z—$L^2$ are selected from the structures of the formulae (2) to (12),

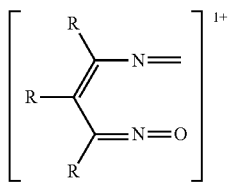
formula (2)

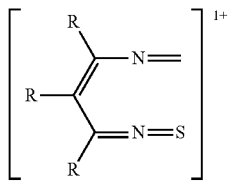
formula (3)

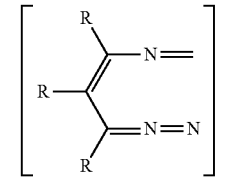
formula (4)

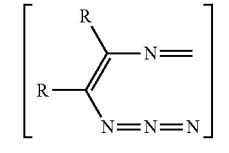
formula (5)

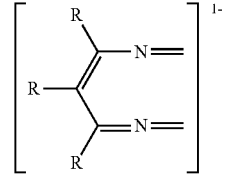
formula (6)

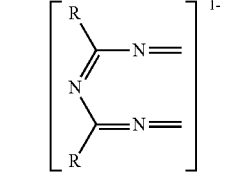
formula (7)

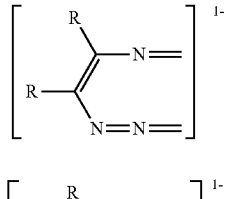
formula (8)

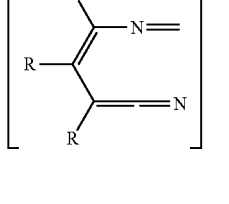
formula (9)

-continued

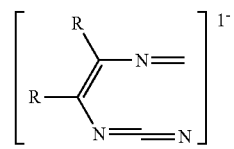
formula (10)

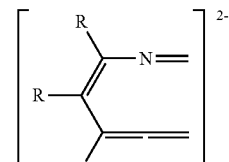
formula (11)

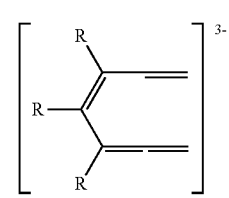
formula (12)

where R has the same meaning as defined in claim 1.

11. The compound according to claim 1, wherein two or more adjacent radicals R with one another or R with $R^1$ form an aromatic ring.

12. The compound according to claim 1, wherein $M^1$ and $M^2$ is selected, identically or differently on each occurrence, from the group consisting of Pt(II), Pd(II), Ni(II), Ir(I), Rh(I), Cu(I), Ag(I) and Au(I);

$L^1$—X—Y—Z—$L^2$ is an anionic ligand;

X, Y and Z is, identically or differently on each occurrence, CR or N, with the proviso that a maximum of one of the groups X, Y and Z stands for N;

$L^1$ and $L^2$ is selected, identically or differently on each occurrence, from the group consisting of —NC, —NN and —CC;

R, if R, for X or Z=CR, is bonded to X or Z respectively, is selected, identically or differently on each occurrence, from the group consisting of $Si(R^1)_3$, a straight-chain alkyl group having 1 to 20 C atoms or a straight-chain alkenyl or alkynyl group having 2 to 20 C atoms or a branched or cyclic alkyl, alkenyl or alkynyl group having 3 to 20 C atoms, each of which is optionally substituted by one or more radicals $R^1$, where one or more non-adjacent $CH_2$ groups is optionally replaced by $R^1C=CR^1$ or C≡C or O and where one or more H atoms is optionally replaced by D or F, or an aromatic or heteroaromatic ring system having 5 to 30 aromatic ring atoms, which optionally in each case be substituted by one or more radicals $R^1$, or an aralkyl or heteroaralkyl group having 5 to 30 aromatic ring atoms, which optionally in each case be substituted by one or more radicals $R^1$; two adjacent radicals R or one radical R with a radical $R^1$ here may also form a mono- or polycyclic, aliphatic, aromatic and/or benzo-fused ring system with one another;

p is 2, 3, or 4;

and the other symbols and indices have the meanings given in claim 1.

13. The compound according to claim 1, wherein the $L^3$ is carbon monoxide, nitrogen monoxide, isonitrile, amine, phosphine, phosphite, arsine, stibine, ether, aliphatic or aromatic sulfide, aliphatic or aromatic selenide, hydride, deuteride, the halides F, Cl, Br and I, azide, alkylacetylide, aryl- or heteroarylacetylide, alkyl, aryl, hydroxide, cyanide, cyanate, isocyanate, thiocyanate, isothiocyanate, aliphatic or aromatic alcoholates, aliphatic or aromatic thioalcoholates, amide, carboxylate, nitrogen-containing heterocycle, aliphatic and aromatic phosphide $PR_2^-$, or aliphatic or aromatic selenides $SeR^-$, $O^{2-}$, $S^{2-}$, nitrene, which result in coordination in the form R-N=M, $N^{3-}$, diamine, imine, diimine, diphosphine, 1,3-diketonates derived from 1,3-diketone, 3-ketonates derived from 3-ketoesters, carboxylates derived from aminocarboxylic acids, salicyliminates derived from salicylimines, dialcoholates derived from dialcohols, dithiolates derived from dithiols, and bidentate monoanionic ligands which have with the metal a cyclometallated five-membered ring or six-membered ring having at least one metal-carbon bond;

and in that the ligands $L^4$ are selected, identically or differently on each occurrence, from the group consisting of H, O, S, Se, CO, C≡N, NO, alkyl group, C(=$CR_2$), —CR=CR—, ortho-phenylene, bisphosphide, bissulfide, bisphosphine, bisamine, bisamide, carbonate, thiocarbonate, isonitrile, acetylide, thiocarbonyl, or ligands of the formulae (44) to (51):

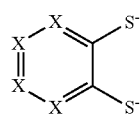

formula (44)

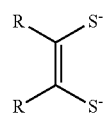

formula (45)

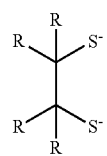

formula (46)

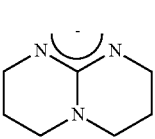

formula (47)

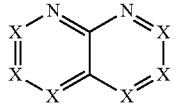

formula (48)

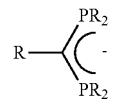

formula (49)

formula (50)

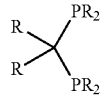

formula (51)

where the symbols and indices used have the meanings given in claim 1.

14. The compound according to claim 1, wherein the $L^3$ is a cyclometallated five-membered ring.

15. An electronic device which comprises the compound according to claim 1.

16. The electronic device as claimed in claim 15, wherein the electronic device is selected from the group consisting of organic electroluminescent device, organic integrated circuit, organic field-effect transistor, organic thin-film transistor, organic light-emitting transistor, organic solar cell, organic optical detector, organic photoreceptor, organic field-quench device, light-emitting electrochemical cell or organic laser diode.

17. An organic electroluminescent device which comprises the compound according to claim 1 is present as emitting compound in an emitting layer.

18. An organic electroluminescent device which comprises the compound according to claim 1 is present as emitting compound in an emitting layer, and in combination with one or more matrix materials.

\* \* \* \* \*